(12) United States Patent
Lee et al.

(10) Patent No.: US 10,688,473 B2
(45) Date of Patent: *Jun. 23, 2020

(54) LIGAND COMPOUND, ORGANIC CHROMIUM COMPOUND, CATALYST SYSTEM FOR OLIGOMERIZATION OF OLEFINS, AND METHOD FOR OLIGOMERIZING OLEFINS USING THE SAME

(71) Applicant: LG CHEM, LTD., Seoul (KR)

(72) Inventors: Yong Ho Lee, Daejeon (KR); Eun Ji Shin, Daejeon (KR); Jin Young Park, Daejeon (KR); Seok Pil Sa, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 100 days.

This patent is subject to a terminal disclaimer.

(21) Appl. No.: 15/518,431

(22) PCT Filed: Dec. 2, 2015

(86) PCT No.: PCT/KR2015/013077
§ 371 (c)(1),
(2) Date: Apr. 11, 2017

(87) PCT Pub. No.: WO2016/093548
PCT Pub. Date: Jun. 16, 2016

(65) Prior Publication Data
US 2017/0312738 A1    Nov. 2, 2017

(30) Foreign Application Priority Data

Dec. 11, 2014 (KR) ......................... 10-2014-0178771
May 26, 2015 (KR) ......................... 10-2015-0073180
Dec. 1, 2015 (KR) ......................... 10-2015-0169714

(51) Int. Cl.
| | |
|---|---|
| B01J 23/26 | (2006.01) |
| C07F 11/00 | (2006.01) |
| C07C 2/36 | (2006.01) |
| B01J 31/18 | (2006.01) |
| C07F 9/90 | (2006.01) |
| C07F 9/66 | (2006.01) |
| C07F 9/02 | (2006.01) |
| C07F 9/46 | (2006.01) |
| C07F 9/50 | (2006.01) |
| C07F 9/70 | (2006.01) |
| C08F 4/78 | (2006.01) |

(52) U.S. Cl.
CPC ............ *B01J 23/26* (2013.01); *B01J 31/188* (2013.01); *C07C 2/36* (2013.01); *C07F 9/02* (2013.01); *C07F 9/46* (2013.01); *C07F 9/50* (2013.01); *C07F 9/66* (2013.01); *C07F 9/70* (2013.01); *C07F 9/90* (2013.01); *C07F 11/00* (2013.01); *C08F 4/78* (2013.01); *B01J 2231/20* (2013.01); *B01J 2531/62* (2013.01); *C07C 2523/26* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 7,141,633 | B2 | 11/2006 | Wass |
| 7,786,336 | B2 | 8/2010 | Zhang et al. |
| 7,829,749 | B2 | 11/2010 | Gao et al. |
| 7,964,763 | B2 | 6/2011 | Dixon et al. |
| 8,076,523 | B2 | 12/2011 | Bollmann et al. |
| 8,309,779 | B2 | 11/2012 | Han et al. |
| 2007/0232481 | A1 | 10/2007 | Zhang et al. |
| 2008/0027188 | A1 | 1/2008 | Small et al. |
| 2009/0270635 | A1 | 10/2009 | Yamano et al. |
| 2010/0298618 | A1 | 11/2010 | Aliyev et al. |
| 2012/0172645 | A1 | 7/2012 | Sydora |
| 2012/0310025 | A1 | 12/2012 | Wang et al. |
| 2012/0316303 | A1 | 12/2012 | Hanton et al. |
| 2016/0045906 | A1 | 2/2016 | Sa et al. |
| 2016/0122371 | A1 | 5/2016 | Lee et al. |
| 2016/0207946 | A1 | 7/2016 | Eun Ji et al. |
| 2016/0271600 | A1 | 12/2016 | Sa et al. |
| 2017/0029346 | A1 | 2/2017 | Lee et al. |

FOREIGN PATENT DOCUMENTS

| | | |
|---|---|---|
| CN | 1651142 A | 8/2005 |
| CN | 103044181 A | 4/2013 |
| CN | 103285926 A | 9/2013 |
| CN | 104511311 A | 4/2015 |

(Continued)

OTHER PUBLICATIONS

Cloete et al., Inorganic Chemistry, Ethylene Tri- and Tetramerization; a Steric Parameter Selectivity Switch from X-ray Cystallography and Computational Analysis, 2013, vol. 52, No. 5, pp. 2268-2270.
Zhang, et al.: "Synthesis of Diphenylphosphinoamine Ligands and Their Catalytic Performance for Ethylene tetramerization with Cr(III) Compounds", Chinese Journal of Catalysis, vol. 27, No. 5, May 27, 2006, pp. 416-420.
Chinese Science Bulletin 2006 vol. 51 No. 5 521-523.
Journal of Catalysis, 2007, vol. 249, No. 2, pp. 244-249.

(Continued)

*Primary Examiner* — Yuan Qian
(74) *Attorney, Agent, or Firm* — Dentons US LLP

(57) ABSTRACT

The present invention relates to a ligand compound, a catalyst system for oligomerization of olefins including the ligand compound and the organic chromium compound, and a method for oligomerizing olefins using the same. The catalyst system for olefin oligomerization according to the present invention invention exhibits high selectivity to 1-hexene or 1-octene while having excellent catalytic activity, thereby enabling more efficient production of alpha-olefins.

6 Claims, No Drawings

(56) References Cited

FOREIGN PATENT DOCUMENTS

| | | |
|---|---|---|
| KR | 101108388 B1 | 1/2012 |
| KR | 1020120098711 A | 9/2012 |
| KR | 101311122 B1 | 9/2013 |
| KR | 101445431 B1 | 9/2014 |
| KR | 1020150057988 A | 5/2015 |
| KR | 1020150058018 A | 5/2015 |
| WO | 2010092554 A1 | 8/2010 |
| WO | 2016/129848 A1 | 8/2016 |
| WO | 2016/186287 A1 | 11/2016 |
| WO | 2016/186291 A1 | 11/2016 |
| WO | 2016/200000 A1 | 12/2016 |

OTHER PUBLICATIONS

Journal of Organometallic Chemistry, 2009, vol. 694, No. 5, pp. 731-736.
Organometallics, 2002, vol. 21, No. 20, pp. 4241-4248.
Polyhedron, 2006, vol. 25, No. 16, pp. 3133-3137.
Polymer Chemistry, 2012, vol. 57, No. 13, pp. 1510-1515.
Inorg. Chem., 2008, vol. 47, No. 7, pp. 2608-2612.
Inorg. Chem., 1967, vol. 6, No. 10, pp. 1765-1769.
Inorg. Chem., 2012, vol. 51, No. 2, pp. 874-881.

LIGAND COMPOUND, ORGANIC CHROMIUM COMPOUND, CATALYST SYSTEM FOR OLIGOMERIZATION OF OLEFINS, AND METHOD FOR OLIGOMERIZING OLEFINS USING THE SAME

CROSS-REFERENCE TO RELATED APPLICATION(S)

This application is a National Stage Application of International Application No. PCT/KR2015/013077, filed Dec. 2, 2015, and claims the benefit of Korean Patent Application No. 10-2015-0169714, filed on Dec. 1, 2015, Korean Patent Application No. 10-2015-0073180, filed on May 26, 2015 and Korean Patent Application No. 10-2014-0178771, filed on Dec. 11, 2014, the contents of which are incorporated herein by reference in their entirety for all purposes as if fully set forth below.

TECHNICAL FIELD

The present invention relates to a ligand compound, an organic chromium compound, a catalyst system for oligomerization of olefins including the ligand compound and the organic chromium compound, and a method for oligomerizing olefins using the same.

BACKGROUND

Linear alpha-olefins such as 1-hexene, 1-octene, and the like are used in a detergent, a lubricant, a plasticizer, and so on, and particularly, are widely used as a comonomer for adjusting the density of a polymer during the preparation of linear low density polyethylene (LLDPE).

Such linear alpha-olefins have been mostly prepared through a Shell higher olefin process. However, since the method synthesizes alpha-olefins of various lengths together according to Schultz-Flory distribution, there is an inconvenience of requiring an additional separation process in order to obtain a specific alpha-olefin.

In order to resolve these problems, a method of selectively synthesizing 1-hexene through a trimerization reaction of ethylene and a method of selectively synthesizing 1-octene through tetramerization of ethylene have been suggested. Further, various studies on catalyst systems enabling such selective oligomerization of ethylene have been undertaken.

However, the previously known catalyst systems have a problem in that the selectivity to 1-hexene, 1-octene or the like is not sufficient, or the catalytic activity for oligomerization is poor.

SUMMARY OF THE INVENTION

The present invention provides a novel ligand compound capable of exhibiting high catalytic activity and selectivity in the oligomerization reaction of olefins.

The present invention further provides a novel organic chromium compound capable of exhibiting high catalytic activity and selectivity in the oligomerization reaction of olefins.

The present invention further provides a catalyst system for oligomerization of olefins including the ligand compound or the organic chromium compound.

The present invention further provides a method for oligomerizing olefins using the catalyst system According to the present invention, there is provided a ligand compound, including two or more groups represented by the following chemical formula 1 in a molecule, and including a linker connecting between respective groups represented by the chemical formula 1 by one or two consecutive carbon-carbon bonds, wherein the linker is a branched alkylene group or alkenylene group having 3 to 10 carbon atoms which may or may not contain one or more heteroatoms:

[Chemical Formula 1]

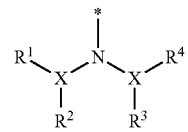

in the chemical formula 1,
N is nitrogen,
each of X is independently phosphorus (P), arsenic (As) or antimony (Sb),
$R^1$ to $R^4$ are each independently a hydrocarbyl group or a heterohydrocarbyl group, and
* represents a binding site, and a solid line represents a covalent bond.

Further, according to the present invention, there is provided an organic chromium compound including two or more groups represented by the following chemical formula 1' in a molecule, and a linker connecting between respective groups represented by the chemical formula 1' by one or two consecutive carbon-carbon bonds, wherein the linker is a branched alkylene group or alkenylene group having 3 to 10 carbon atoms which may or may not contain one or more heteroatoms:

[Chemical Formula 1']

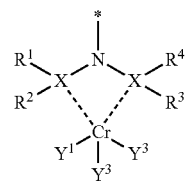

in the chemical formula 1',
N is nitrogen,
each of X is independently phosphorus (P), arsenic (As) or antimony (Sb),
$R^1$ to $R^4$ are each independently a hydrocarbyl group or a heterohydrocarbyl group,
Cr is chromium,
$Y^1$ to $Y^3$ are each independently a halogen, a hydrogen, a hydrocarbyl group having 1 to 10 carbon atoms, or a heterohydrocarbyl group having 1 to 10 carbon atoms,
* represents a binding site, a solid line represents a covalent bond, and a dotted line represents a coordinate bond.

Furthermore, according to the present invention, there is provided a catalyst system for oligomerization of olefins including:
i) a chromium source; the ligand compound; and a cocatalyst, or
ii) the organic chromium compound; and a cocatalyst.

In addition, according to the present invention, there is provided a method for oligomerizing olefins, comprising the step of conducting an oligomerization reaction of olefins in the presence of the catalyst system to form alpha-olefins.

Advantageous Effects

The catalyst system for oligomerization of olefins according to the present invention exhibits high selectivity to 1-hexene or 1-octene while having excellent catalytic activity, thereby enabling more efficient production of alpha-olefins.

DETAILED DESCRIPTION OF THE EMBODIMENTS

Hereinafter, the ligand compound, the organic chromium compound, the catalyst system for oligomerization of olefins, and the method for oligomerizing olefins using the same according to embodiments of the present invention will be described in more detail.

The technical terms used in the present specification are only for mentioning specific embodiments, and are not intended to limit the present invention unless there is a particular mention about them. The singular expressions used herein may include the plural expressions unless they are differently expressed contextually. The meaning of the term "include" used in the specification embodies specific characteristics, areas, integers, steps, actions, elements and/or components, and does not exclude existence or addition of other specific characteristics, areas, integers, steps, actions, elements, components and/or groups.

In the present specification, "catalyst system" means what can be obtained as the catalyst composition having activity by mixing 3 components including a chromium source, a ligand compound, and a cocatalyst, or alternatively 2 components of an organic chromium compound and a cocatalyst, at the same time or in an arbitrary order. Said 3 components or 2 components of the catalyst system may be mixed in the presence or absence of a proper solvent and a monomer, and may be used in the form of being supported or unsupported.

According to one embodiment of the present invention, there is provided a ligand compound, including two or more groups represented by the following chemical formula 1 in a molecule, and including a linker connecting between respective groups represented by the chemical formula 1 by one or two consecutive carbon-carbon bonds, wherein the linker is a branched alkylene group or alkenylene group having 3 to 10 carbon atoms which may or may not contain one or more heteroatoms:

[Chemical Formula 1]

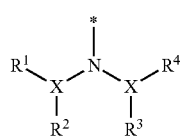

in the chemical formula 1,

N is nitrogen, each of X is independently phosphorus (P), arsenic (As) or antimony (Sb), and $R^1$ to $R^4$ are each independently a hydrocarbyl group or a heterohydrocarbyl group.

As the result of successive experiments of the present inventors, it has been found that, when a ligand compound satisfying the above structure is applied for a catalyst system for oligomerization of olefins, it not only exhibits excellent catalytic activity, but also exhibits high selectivity to alpha-olefins such as 1-hexene or 1-octene, thereby enabling more effective preparation of alpha-olefins.

According to an embodiment of the present invention, the ligand compound includes two or more groups (for example, diphosphino aminyl moiety) represented by the chemical formula 1 in the molecule, and has a linker connecting between respective groups represented by the chemical formula 1 by one or two consecutive carbon-carbon bonds. Such a linker may be a branched alkylene group or alkynylene group having 3 to 10 carbon atoms, more specifically, a branched alkylene group having 3 to 8 carbon atoms.

More specifically, the linker, which can be a branched alkylene group having 3 to 8 carbon atoms, may have a structure of a branched alkylene group in which one or more carbons contained in the alkylene group is further substituted with an alkyl group having 1 to 5 carbon atoms, while connecting between nitrogens of the group represented by the chemical formula (1) by an alkyl group having 2 or 3 carbon atoms (one or two consecutive carbon-carbon bonds), as shown in the chemical formula 3 to 4 below:

[Chemical Formula 3]

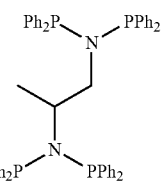

[Chemical Formula 4]

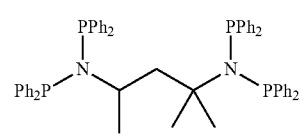

These linkers may connect between two or more groups of the chemical formula 1 over a relatively short distance (one or two consecutive carbon-carbon bonds), compared to structures such as known linkers, ligand compounds or organic chromium compounds, and they can have structural characteristics with great flexibility, compared with other types of linkers containing aromatic rings or aliphatic rings. As a result, in the case of applying the ligand compound of one embodiment and the organic chromium compound obtained therefrom, the mutually adjacent groups of the chemical formula 1 and adjacent chromium active sites can more easily interact in the process of oligomerization of olefin (ethylene). Furthermore, it is predicted that olefins (ethylene) bound to each active site can very easily interact and bind. Therefore, when the ligand compound or the like of one embodiment described above is applied, not only higher activity can be exhibited for oligomerization of olefin (ethylene) but also 1-hexene or 1-octene which are trimerization or tetramerization products through the oligomerization can be obtained with higher selectivity.

On the other hand, the ligand compound according to one embodiment of the invention will be described in more detail as follows.

First, the ligand compound has two or more groups represented by the chemical formula 1. Respective groups represented by the chemical formula 1 are connected by the above-described linker.

In the chemical formula 1, N is nitrogen.

In the chemical formula 1, each of X may be independently phosphorus (P), arsenic (As), or antimony (Sb). Preferably, the group represented by the chemical formula 1 may be a diphosphino aminyl moiety in which each of X is phosphorus (P).

In the chemical formula 1, $R^1$ to $R^4$ may be each independently a hydrocarbyl group or a heterohydrocarbyl group. Here, the hydrocarbyl group is a monovalent group formed by removing a hydrogen atom from a hydrocarbon. Further, the heterohydrocarbyl group is a monovalent group formed by removing a hydrogen atom from a hydrocarbon containing a hetero atom.

As a non-limiting example, the $R^1$ to $R^4$ may be each independently a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group. Here, at least one hydrogen included in the alkyl group, the cycloalkyl group, the aryl group, the aralkyl group, and the alkoxy group may be substituted with a $C_1$-$C_{10}$ alkyl group, a $C_1$-$C_{10}$ alkoxy group, a halogen group, or a cyano group.

More specifically, the $R^1$ to $R^4$ may be each independently methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, m-methylphenyl, m-ethylphenyl, m-isopropylphenyl, m-t-butylphenyl, m-methoxyphenyl, m-isopropoxyphenyl, p-methylphenyl, p-ethylphenyl, p-isopropylphenyl, p-t-butylphenyl, p-methoxyphenyl, p-isopropoxyphenyl, cumyl, mesityl, biphenyl, naphthyl, anthracenyl, methoxy, ethoxy, phenoxy, tolyloxy, dimethylamino, thiomethyl, or trimethylsilyl group.

In the ligand compound, the two or more groups represented by the chemical formula 1 are connected by a linker connecting between nitrogen atoms of the respective groups by one or two consecutive carbon-carbon bonds. In particular, according to an embodiment of the invention, the linker is a branched alkyl group or alkenyl group having 3 to 10 carbon atoms, more specifically, a branched alkylene group having 3 to 8 carbon atoms. In the most specific example, the linker not only connects between nitrogens of the groups represented by the chemical formula 1 by an alkylene group having 2 or 3 carbon atoms (one or two continuous carbon-carbon bonds), but also may be a branched alkylene group in which one or more carbons contained in the alkylene group are further substituted by at least one alkyl group having 1 to 5 carbon atoms.

The above-mentioned ligand compound is a compound having two groups represented by the chemical formula 1 in the molecule, and may be a compound represented by the following chemical formula 2:

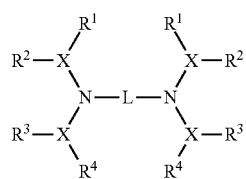

[Chemical Formula 2]

in the chemical formula 2,

L is a linker connecting between nitrogen (N) atoms by one or two consecutive carbon-carbon bonds, and is a branched alkylene group or alkenylene group having 3 to 10 carbon atoms which may or may not contain one or more heteroatoms, each of X is independently phosphorus (P), arsenic (As) or antimony (Sb), and $R^1$ to $R^4$ are each independently a hydrocarbyl group or a heterohydrocarbyl group.

In addition, most specific examples of the above-mentioned ligand compounds include compounds represented by the following chemical formula (3) or (4):

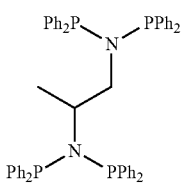

[Chemical Formula 3]

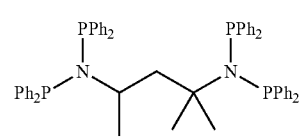

[Chemical Formula 4]

The ligand compound may be realized with various combinations within a range fulfilling the aforementioned requirements, in addition to the above examples. Further, the ligand compound may be synthesized by applying known reactions.

According to another embodiment of the present invention, there is provided an organic chromium compound including two or more groups represented by the following chemical formula 1' in a molecule, and a linker connecting between respective groups represented by the chemical formula 1' by one or two consecutive carbon-carbon bonds, wherein the linker is a branched alkylene group or alkenylene group having 3 to 10 carbon atoms which may or may not contain one or more heteroatoms:

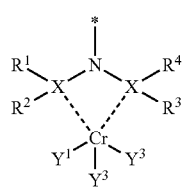

[Chemical Formula 1']

in the chemical formula 1',

N is nitrogen, each of X is independently phosphorus (P), arsenic (As) or antimony (Sb), $R_1$ to $R_4$ are each independently a hydrocarbyl group or a heterohydrocarbyl group, Cr is chromium, $Y^1$ to $Y^3$ are each independently a halogen, a hydrogen, a hydrocarbyl group having 1 to 10 carbon atoms, or a heterohydrocarbyl group having 1 to 10 carbon atoms,

* represents a binding site, a solid line represents a covalent bond, and a dotted line represents a coordinate bond.

The organic chromium compound is a chromium complex compound of the above-mentioned ligand compound, and has a form wherein a chromium atom included in a chromium source is coordinated with two X included in the group represented by the chemical formula 1. Such an organic chromium compound may be applied for a catalyst system for oligomerization of olefins to exhibit improved catalytic activity and high selectivity to 1-hexene or 1-octene.

On the other hand, in the chemical formula 1', the explanation and specific examples of X and $R^1$ to $R^4$ are as defined in the chemical formula 1 above. Further, in the chemical formula 1', Cr is chromium, the $Y^1$, $Y^2$ and $Y^3$ are each independently halogen, hydrogen, a hydrocarbyl group having 1 to 10 carbon atoms, or a heterohydrocarbyl group having 1 to 10 carbon atoms.

Specifically, the organic chromium compound may be represented by the following chemical formula 2':

[Chemical Formula 2']

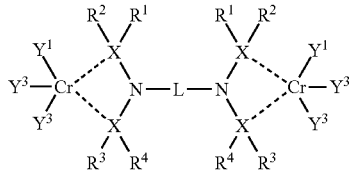

in the chemical formula 2',

L is a linker connecting between nitrogen (N) atoms by one or two consecutive carbon-carbon bonds, and is a branched alkylene group or alkenylene group having 3 to 10 carbon atoms which may or may not contain one or more hetero atoms, each of X is independently phosphorus (P), arsenic (As) or antimony (Sb), $R^1$ to $R^4$ are each independently a hydrocarbyl group or a heterohydrocarbyl group, Cr is chromium, $Y^1$ to $Y^3$ are each independently a halogen, a hydrogen, a hydrocarbyl group having 1 to 10 carbon atoms, or a heterohydrocarbyl group having 1 to 10 carbon atoms.

In the chemical formula 2', L may be a branched alkylene group or alkenylene group having 3 to 10 carbon atoms, more specifically, a branched alkylene group having 3 to 8 carbon atoms, as described with respect to the ligand compound of one embodiment. In the most specific example, it not only connects between nitrogens of the groups represented by the chemical formula 1 by an alkylene group having 2 or 3 carbon atoms (one or two continuous carbon-carbon bonds), but also may be a branched alkylene group in which one or more carbons contained in the alkylene group are further substituted by at least one alkyl group having 1 to 5 carbon atoms.

In addition, the organic chromium compound of the chemical formula 1' may be formed by a conventional method of reacting the ligand compound with a chromium source.

According to another embodiment of the invention, there is provided a catalyst system for oligomerization of olefins including the above-mentioned ligand compound or organic chromium compound.

As one example, the catalyst system for oligomerization of olefins includes a chromium source; a ligand compound of one embodiment as described above; and a cocatalyst. As another example, the catalyst system for oligomerization of olefins may include an organic chromium compound of another embodiment as described above; and a cocatalyst. That is, according to an embodiment of the invention, the catalyst system for oligomerization of olefins may be i) a three-component catalyst system including a chromium source, the above-described ligand compound, and a cocatalyst, or ii) a two-component catalyst system including the above-described organic chromium compound and a cocatalyst.

In the catalyst system, the chromium source may be an organic or inorganic chromium compound with an oxidation state of chromium of 0 to 6, for example, a chromium metal, or a compound wherein any organic or inorganic radical is bonded to chromium. Herein, the organic radical may be an alkyl, an alkoxy, an ester, a ketone, an amido, a carboxylate radical, and the like, which have 1 to 20 carbon atoms per radical, and the inorganic radical may be a halide, sulfate, oxide, and the like.

More specifically, the chromium source is a compound that can exhibit high activity for oligomerization of olefins and can be easily used and acquired, and may be one or more compounds selected from the group consisting of chromium (III) acetylacetonate, chromium(III) chloride tetrahydrofuran, chromium(III) 2-ethylhexanoate, chromium(III) acetate, chromium(III) butyrate, chromium(III) pentanoate, chromium(III) laurate, chromium(III) tris(2,2,6,6-tetramethyl-3,5-heptanedionate), and chromium(III) stearate.

In addition, the cocatalyst is an organometallic compound including a Group 13 metal, and may be applied without particular limitation as long as it can be generally used for polymerization of olefins in the presence of a transition metal catalyst.

For example, the cocatalyst may be one or more compounds selected from the group consisting of compounds represented by the following chemical formulae 4 to 6.

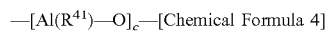  [Chemical Formula 4]

In the chemical formula 4, each $R^{41}$ is the same as or different from each other and are independently a halogen radical, a $C_1$-$C_{20}$ hydrocarbyl radical, or a $C_1$-$C_{20}$ hydrocarbyl radical substituted with a halogen, and c is an integer of 2 or more.

  [Chemical Formula 5]

In the chemical formula 5, D is aluminum or boron, and $R^{51}$ is a $C_1$-$C_{20}$ hydrocarbyl or a $C_1$-$C_{20}$ hydrocarbyl substituted with a halogen.

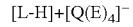  [Chemical Formula 6]

In the chemical formula 6,

L is a neutral Lewis base, $[L-H]^+$ is a Bronsted acid, Q is boron or aluminum of a +3 oxidation state, and each of E is independently a $C_6$-$C_{20}$ aryl group or a $C_1$-$C_{20}$ alkyl group of which at least one hydrogen atom is substituted or unsubstituted with a halogen, a $C_1$-$C_{20}$ hydrocarbyl, an alkoxy functional group, or a phenoxy functional group.

In a specific example, the compound represented by the chemical formula 4 may be an alkyl aluminoxane such as methyl aluminoxane, ethyl aluminoxane, isobutyl aluminoxane, butyl aluminoxane, and the like.

Further, the compound represented by the chemical formula 5 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and so on.

Furthermore, the compound represented by the chemical formula 6 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl) aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra (p-trifluoromethylphenyl)borate, triphenylcarbonium tetrapentafluorophenylborate, and so on.

Further, as a non-limiting example, the cocatalyst may be an organoaluminum compound, an organoboron compound, an organomagnesium compound, an organozinc compound, an organolithium compound, or a mixture thereof. Specifically, the cocatalyst is preferably an organoaluminum compound, and more preferably, may be one or more compounds selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, and modified methylaluminoxane.

On the other hand, the content ratio of the components constituting the catalyst system may be determined in consideration of the catalytic activity and the selectivity to linear alpha-olefins. According to one embodiment, when the catalyst system is a three-component catalyst system, it is preferable that the mole ratio of the diphosphino aminyl moiety of the ligand compound:the chromium source:the cocatalyst is controlled to be about 1:1:1 to 10:1:10,000, or about 1:1:100 to 5:1:3,000. Further, when the catalyst system is a two-component catalyst system, it is preferable that the mole ratio of the diphosphino aminyl moiety of the organic chromium compound: the cocatalyst is controlled to be 1:1 to 1:10,000, or 1:1 to 1:5000, or 1:1 to 1:3000.

Further, the components constituting the catalyst system may be mixed at the same time or in an arbitrary order in the presence or absence of a proper solvent and a monomer for acting as an active catalyst system. The proper solvent may be heptane, toluene, cyclohexane, methylcyclohexane, 1-hexene, 1-octene, diethylether, tetrahydrofuran, acetonitrile, dichloromethane, chloroform, chlorobenzene, methanol, acetone, and so on.

Furthermore, according to one embodiment, the catalyst system may further include a supporting material. That is, the ligand compound of one embodiment described above may be applied to the oligomerization of ethylene in the form of being supported on the supporting material. The supporting material may be metals, metal salts, or metal oxides which are applied to a conventional supported catalyst. As non-limiting examples, the supporting material may be silica, silica-alumina, silica-magnesia, and so on, and may include an oxide, a carbonate, a sulfate, or a nitrate component such as $Na_2O$, $K_2CO_3$, $BaSO_4$, $Mg(NO_3)_2$, and so on.

On the other hand, according to still another embodiment of the invention, there is provided a method for oligomerization of olefins, including the step of carrying out the oligomerization reaction of olefins in the presence of the catalyst system to form alpha-olefins.

The method for oligomerization of olefins according to the present invention may be carried out by using olefins (for example, ethylene) as raw material and applying said catalyst system and a common device and contact technology. As non-limiting examples, the oligomerization reaction of olefins may be carried out by a homogeneous liquid phase reaction in the presence or absence of an inert solvent, by a slurry reaction using the catalyst system that is partially or not totally dissolved, by a bulk reaction in which the alpha-olefin, the product, acts as a main medium, or by a gas phase reaction.

Further, the oligomerization reaction of olefins may be carried out in the presence of an inert solvent. As non-limiting examples, the inert solvent may be benzene, toluene, xylene, cumene, chlorobenzene, dichlorobenzene, heptane, cyclohexane, methylcyclohexane, methylcyclopentane, n-hexane, 1-hexene, 1-octene, and so on.

Furthermore, the oligomerization reaction of olefins may be carried out at a temperature of about 0 to 200° C., or about 0 to 150° C., or about 30 to 100° C., or about 50 to 100° C. In addition, the reaction may be carried out at a pressure of about 15 to 3000 psig, or about 15 to 1500 psig, or about 15 to 1000 psig.

The above-mentioned oligomerization reaction can be suitably applied to a method for selective formation of alpha-olefins including 1-hexene, 1-octene or a mixture thereof.

Hereinafter, preferable examples are presented for better understanding the present invention. However, the following examples are only for illustrating the present invention and the present invention is not limited to or by them.

Preparation Example: Synthesis of Ligand Compound

All the reactions were progressed under argon using Schlenk technique or a glovebox. The synthesized ligands were analyzed by $^1H$ (500 MHz) and $^{31}P$ (202 MHz) NMR spectra using a Varian 500 MHz spectrometer. The shifts were expressed in ppm as a downfield from TMS with a residual solvent peak as a reference. The phosphorous probes were calibrated with aqueous $H_3PO_4$.

Preparation Example 1: Synthesis of Compound of Chemical Formula 3

1,2-diaminopropane and triethylamine (3-10 equivalents to 1,2-diaminopropane) were dissolved in dichloromethane (about 50 ml) under an argon (Ar) atmosphere. While the flask was immersed in a water bath, chlorodiphenylphosphine (4 equivalents to 1,2-diaminopropane) was slowly added and stirred overnight. After placing the mixture under vacuum to remove the solvent, diethyl ether (or THF) solvent was added. The mixture was sufficiently stirred, and a triethylammonium chloride salt was removed with an air-free glass filter. Remaining solvent was removed in the filtrate to synthesize a ligand compound of the following chemical formula 3.

[Chemical Formula 3]

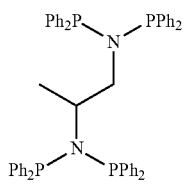

$^{31}$P NMR (202 MHz, CDCl$_3$): 58.5 (s), 50.4/55.8 (broad) ppm

Preparation Example 2: Synthesis of Compound of Chemical Formula 4

A ligand compound of the following chemical formula 4 was synthesized in the same manner in Preparation Example 1, except that 2,4-diamino-4-methylpentane was used instead of 1,2-diaminopropane.

[Chemical Formula 4]

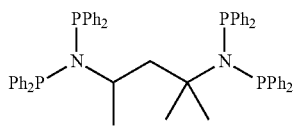

$^{31}$P NMR (202 MHz, CDCl$_3$): 55.0 (broad, s), 47.7 (broad, s) ppm

Comparative Preparation Example 1: Synthesis of Ligand Compound

A ligand compound of the following chemical formula was synthesized in the same manner in Preparation Example 1, except that 2-isopropyl-6-methylaniline was used instead of 1,2-diaminopropane, and chlorodiphenylphosphine (2 equivalents to 2-isopropyl-6-methylaniline) was used.

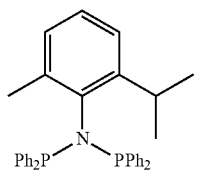

$^{31}$P NMR (202 MHz, CDCl$_3$): 57 ppm

Comparative Preparation Example 2: Synthesis of Ligand Compound

A ligand compound of the following chemical formula was synthesized in the same manner in Preparation Example 1, except that 3,3,5-trimethylcyclohexaneamine was used instead of 1,2-diaminopropane, and chlorodiphenylphosphine (2 equivalents to 3,3,5-trimethylcyclohexaneamine) was used.

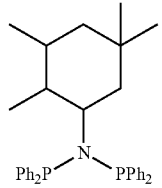

$^{31}$P NMR (202 MHz, CDCl$_3$): 45.5 (br s), 55.5 (br s)

Comparative Preparation Example 3: Synthesis of Ligand Compound

A ligand compound of the following chemical formula was synthesized in the same manner in Preparation Example 1, except that 1,2-diaminoethane was used instead of 1,2-diaminopropane.

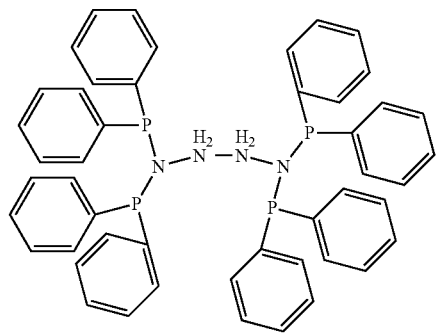

$^{31}$P NMR (202 MHz, CDCl$_3$): 62 ppm

Example 1

Under an argon gas atmosphere, chromium(III) acetylacetonate (17.5 mg, 0.05 mmol) and the ligand compound (0.025 mmol) according to Preparation Example 1 were introduced in a flask, to which 10 ml of cyclohexane was added and the mixture was stirred to prepare a 5 mM (based on Cr) catalyst solution.

A 600 mL Parr reactor was prepared, vacuum was applied at 120° C. for 2 hours, and then, the inside was replaced with argon, and the temperature was decreased to 45° C. Then, 90 ml of cyclohexane and 2 ml of MMAO (isoheptane solution, Al/Cr=1200) were introduced, and 0.5 mL of the catalyst solution (2.5 µmol Cr) was introduced in the reactor. The mixture was stirred at 500 rpm for 2 minutes, and then, a valve of an ethylene line adjusted to 45 bar was opened to fill the inside of the reactor with ethylene, followed by removing heat to 45° C., and stirring at 500 rpm for 15 minutes. The ethylene line valve was closed, the reactor was cooled to 0° C. with a dry ice/acetone bath, and then, non-reacted ethylene was slowly vented, and 0.5 ml of nonane (GC internal standard) was introduced. After stirring for 10 seconds, 2 mL of the liquid part of the reactor was taken and quenched with water, the obtained organic part was filtered with a PTFE syringe filter to make a GC-FID sample. Then, the distribution of liquid product was analyzed by GC. In addition, 400 mL of ethanol/HCl (10 vol % of aqueous 12M HCl solution) was added to the remaining reaction solution, and the mixture was stirred and filtered to analyze the amount of solid. The resulting polymer was dried overnight in a 65° C. vacuum oven.

Example 2

The oligomerization reaction of ethylene was carried out in the same manner as in Example 1, except that a ligand compound according to Preparation Example 2 was used instead of a ligand compound according to Preparation Example 1.

Comparative Example 1

The oligomerization reaction of ethylene was carried out in the same manner as in Example 1, except that a ligand compound according to Comparative Preparation Example 1 was used instead of a ligand compound according to Preparation Example 1.

Comparative Example 2

The oligomerization reaction of ethylene was carried out in the same manner as in Example 1, except that a ligand compound according to Comparative Preparation Example 2 was used instead of a ligand compound according to Preparation Example 1.

Comparative Example 3

The oligomerization reaction of ethylene was carried out in the same manner as in Example 1, except that a ligand compound according to Comparative Preparation Example 3 was used instead of a ligand compound according to Preparation Example 1.

Comparative Example 4

The oligomerization reaction of ethylene was carried out in the same manner as in Example 1, except that a ligand compound was not used.

In the oligomerization reaction of Examples and Comparative Examples below, the catalytic activity and the obtained products were analyzed, and the results of the analysis are summarized in Table 1 below.

Referring to Table 1, it was confirmed that in the case of Examples, higher catalytic activities were exhibited and the sums of selectivities to 1-hexene and 1-octene were high, compared to Comparative Examples.

The invention claimed is:

1. A ligand compound of Chemical Formula 2:

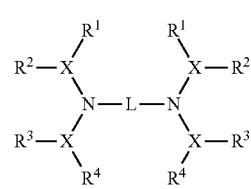

[Chemical Formula 2]

wherein, in Chemical Formula 2:

L is a linker connecting two nitrogen (N) atoms by one or two consecutive carbon-carbon bonds, and is an alkylene or alkenylene group having 2 or 3 carbon atoms, and one or more of the carbon atoms is substituted with an alkyl group having 1 to 5 carbon atoms resulting in a branched alkylene group or alkenylene group having a total of 3 to 10 carbon atoms and which optionally contains one or more hetero atoms;

each X is independently phosphorus (P), arsenic (As) or antimony (Sb); and $R^1$ to $R^4$ are each independently a hydrocarbyl group or a heterohydrocarbyl group.

2. The ligand compound according to claim 1, wherein the linker L is a branched alkylene group having 3 to 8 carbon atoms.

3. The ligand compound according to claim 1, wherein the linker L is a linker connecting two nitrogen (N) atoms by two consecutive carbon-carbon bonds.

4. The ligand compound according to claim 3, wherein the linker L is an alkylene group in which two or more carbons are substituted with an alkyl group having 1 to 5 carbon atoms.

5. The ligand compound according to claim 1, wherein the linker L is an alkylene group in which two or more carbons are substituted with an alkyl group having 1 to 5 carbon atoms.

TABLE 1

| | Ligand | | Example 1 Preparation Example 1 | Example 2 Preparation Example 2 | Comparative Example 1 Comparative Preparation Example 1 | Comparative Example 2 Comparative Preparation Example 2 | Comparative Example 3 Comparative Preparation Example 3 | Comparative Example 4 None |
|---|---|---|---|---|---|---|---|---|
| Catalytic activity (Ton/molCr/hr) | | | 39 | 38 | 21 | 10 | 5.2 | 1.3 |
| alpha- | 1-$C_6$ | 1-$C_6$ | 21.0 | 18.4 | 27.1 | 12.0 | 10.8 | 6.8 |
| olefin | and | 1-$C_8$ | 59.5 | 65.4 | 56.3 | 68.9 | 56.8 | 4.2 |
| (wt %) | 1-$C_8$ | (sum) | 80.5 | 83.8 | 83.4 | 80.9 | 67.6 | 11.0 |
| | 1-$C_{10}$ to 1-$C_{40}$ | | 6.8 | 6.8 | 10.1 | 9.3 | 10 | 20.4 |
| $C_6$ isomers (wt %) | | | 6.5 | 4.1 | 3.9 | 6.6 | 8.9 | 4.1 |
| Poly alpha-olefin (wt %) | | | 4 | 1.4 | 0.5 | 0.1 | 12.3 | 50.7 |

6. A ligand compound of Chemical Formula 3 or 4:
[Chemical Formula 3]
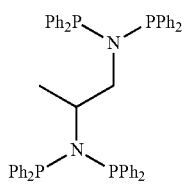
[Chemical Formula 4]
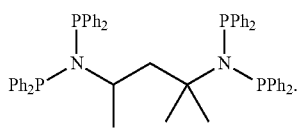
* * * * *